US009332544B2

(12) United States Patent
Lim et al.

(10) Patent No.: US 9,332,544 B2
(45) Date of Patent: May 3, 2016

(54) CHANNEL SWITCHING METHOD IN A MEDICAL BODY AREA NETWORK

(75) Inventors: Jaewon Lim, Gyeonggi-do (KR); Suhwook Kim, Gyeonggi-do (KR); Bonghoe Kim, Gyeonggi-do (KR)

(73) Assignee: LG Electronics Inc., Seoul (KR)

( * ) Notice: Subject to any disclaimer, the term of this patent is extended or adjusted under 35 U.S.C. 154(b) by 100 days.

(21) Appl. No.: 14/009,149

(22) PCT Filed: Mar. 29, 2012

(86) PCT No.: PCT/KR2012/002303
§ 371 (c)(1),
(2), (4) Date: Oct. 1, 2013

(87) PCT Pub. No.: WO2012/141440
PCT Pub. Date: Oct. 18, 2012

(65) Prior Publication Data
US 2014/0036863 A1    Feb. 6, 2014

Related U.S. Application Data

(60) Provisional application No. 61/473,820, filed on Apr. 11, 2011.

(51) Int. Cl.
*H04W 72/04* (2009.01)
*H04W 36/06* (2009.01)
(Continued)

(52) U.S. Cl.
CPC ......... *H04W 72/0453* (2013.01); *H04B 13/005* (2013.01); *H04W 36/06* (2013.01); *A61B 5/0024* (2013.01); *H04W 28/042* (2013.01); *H04W 48/16* (2013.01); *H04W 72/00* (2013.01); *H04W 84/10* (2013.01)

(58) Field of Classification Search
CPC ... H04W 28/042; H04W 72/00; H04W 84/10; H04W 48/16; H04W 36/06; H04W 72/0453; H04B 13/005
See application file for complete search history.

(56) References Cited

U.S. PATENT DOCUMENTS

2003/0171116 A1* 9/2003 Soomro ................. 455/434
2006/0271703 A1* 11/2006 Kim et al. ................. 709/239
(Continued)

FOREIGN PATENT DOCUMENTS

EP              2227046 A1    9/2010
KR    10-2005-0074814 A    7/2005
(Continued)

OTHER PUBLICATIONS

International Search Report issued in corresponding International Patent Application No. PCT/KR2012/002303 dated Oct. 25, 2012.
(Continued)

*Primary Examiner* — Yemane Mesfin
*Assistant Examiner* — Abdelillah Elmejjarmi
(74) *Attorney, Agent, or Firm* — Morgan, Lewis & Bockius LLP

(57) ABSTRACT

The disclosure of the present invention provides a method for a Medical Body Area Network (MBAN) to control, through a master, the channel switching of an MBAN terminal that uses a channel of a first frequency band in an MBAN system. The method includes: receiving information related to the use of each channel of a second frequency band from an MBAN controller; and transmitting information on a channel of the second frequency band that the MBAN terminal is to switch on the basis of the received information related to the use of each channel of the second frequency band. The first frequency band and the second frequency band are distinguished from each other based on whether the MBAN terminal uses a corresponding frequency band first.

4 Claims, 13 Drawing Sheets

(a)

(b)

(51) Int. Cl.
  *H04B 13/00* (2006.01)
  *H04W 28/04* (2009.01)
  *H04W 48/16* (2009.01)
  *H04W 72/00* (2009.01)
  *H04W 84/10* (2009.01)
  *A61B 5/00* (2006.01)

(56) References Cited

U.S. PATENT DOCUMENTS

| | | |
|---|---|---|
| 2007/0104139 A1* | 5/2007 | Marinier et al. .............. 370/329 |
| 2010/0093360 A1 | 4/2010 | Choi et al. |
| 2010/0260162 A1 | 10/2010 | Batra et al. |

FOREIGN PATENT DOCUMENTS

| | | | |
|---|---|---|---|
| KR | 10-0804843 B1 | 2/2008 | |
| KR | 10-2010-0040591 A | 4/2010 | |
| KR | 10-0959326 B1 | 5/2010 | |
| WO | WO2011128795 A1 * | 10/2011 | ............ H04W 16/14 |

OTHER PUBLICATIONS

Office Action dated May 22, 2015, issued by the Korean Intellectual Property Office in Korean Patent Application No. 10-2013-7022949.

* cited by examiner (a)　　　　　　　　　　　　(b)

FIG. 4

| Frame Control | Sequence Number | Addressing Fields | Auxiliary Security header | SuperFrame Specification | GTS fields | Pending address fields | Beacon Payload | FCS |
|---|---|---|---|---|---|---|---|---|

FIG. 8A

| Channel Switching Method | Recommended Channel List | Remaining Time |

FIG. 8B

| Channel Switching Method | Channel No. | Remaining Time |
|---|---|---|

FIG. 8C

| Channel Switching Method | Recommended Channel List | Channel No. | Remaining Time |
|---|---|---|---|

FIG. 9

| Frame Control | Sequence Number | Addressing Fields | Auxiliary Security header | SuperFrame Specification | Channel Switching Method | Recommended Channel List | Remaining Time | GTS fields | Pending address fields | Beacon Payload | FCS |

FIG. 10

| Frame Control | Sequence Number | Addressing Fields | Auxiliary Security header | Channel Switching Method | Recommended Channel List | Remaining Time | Frame Payload | FCS |

CHANNEL SWITCHING METHOD IN A MEDICAL BODY AREA NETWORK

TECHNICAL FIELD

The present invention concerns a channel switching method and apparatus, and more specifically, to a method and apparatus for switching a terminal in a medical body area network (MBAN) to a channel having a different frequency band.

BACKGROUND ART

The medical body area network (MBAN) system has been devised to provide a flexible platform for wireless networking of multiple sensors used for monitoring a patient's physiological data in a healthcare facility, such as a hospital.

The MBAN system operates in a band of 2360 MHz to 240 MHz based on IEEE 802.15.4 and its maximum emission bandwidth is restricted to 5 MHz.

The transmission power of the MBAN system, when operating in 2360 to 2390 MHz, has the smaller one of 1 mW and 10*log(B) dBm. At this time, B is 20 dB emission bandwidth. When operating in 230 to 2400 MHz, the MBAN system uses the smaller value of 20 mW and 10*log(B) dBm as its transmission power. At this time, B is 20 dB emission bandwidth.

2360 to 2400 MHz is a frequency band allocated for another wireless communication system, and the MBAN system operates based on wireless recognition technology. This wireless recognition technology refers to a communication technology in which a network or wireless communication apparatus actively senses and determines the ambient communication environment to adaptively vary transmission/reception characteristics, such as frequency band, transmission power, and encoding scheme, for the optimal communication. At this time, the wireless recognition apparatus, upon sensing the use of other licensed users or primary users in the frequency band the device intends to use, is operated not to interfere with the communication of the other users, among others.

For such purpose, in the MBAN, in the case of operation in a band of 2360 to 2390 MHz, MBAN apparatuses operate in a registered healthcare facility, in principle. In other words, the use of 2360 to 230 MHz should be controlled in cooperation with other licensed users, and when the other licensed users use the corresponding band, all the operations should be initialized in this band, and the operations should be resumed by newly using a band of 2390 to 2400 MHz.

When the MBAN apparatuses move to the outside, their operation should be stopped or their transmission band needs to be changed to a band of 2390 to 2400 MHz that is used as a basic band before transmission. When operating in 2390 to 2400 MHz, the MBAN apparatuses may be used without a limitation on whether it is located indoors or outdoors.

In the conventional MBAN system, a definition has been yet to be made on a method of switching a channel used in one of the 2360 to 2390 MHz band and the 2390 to 2400 MHz band to the other band when the above-described situation occurs.

DETAILED DESCRIPTION OF INVENTION

Technical Problems

Accordingly, an object of this disclosure is to suggest a channel switching method for an MBAN. Another object of this disclosure is to provide an apparatus for performing the method.

Technical Solutions

To achieve the above objects, according to an embodiment of the present invention, a method of controlling channel switching of an MBAN (Medical Body Area Network) terminal using a channel of a first frequency band by an MBAN master in an MBAN system is provided. The method comprises receiving information related to use of each channel of a second frequency band from an MBAN controller; and transmitting an information on a channel of the second frequency band to which the MBAN terminal is to be switched based on the received information related to each channel of the second frequency band, wherein the first frequency band and the second frequency band are separated from each other based on whether the MBAN terminal may first use a frequency of a corresponding band.

The first frequency band may be a frequency band between 2360 MHz and 2390 MHz, and the second frequency band may be a frequency band between 2390 MHz and 2400 MHz.

The channel switching may occur when the first frequency band is used by a wireless communication system other than the MBAN system or when the MBAN terminal moves to an outside of a designated area.

The first frequency band may be a frequency band between 2390 MHz and 2400 MHz, and the second frequency band may be a frequency band between 2360 MHz and 2390 MHz.

The channel switching may occur when the second frequency band is not used by a wireless communication system other than the MBAN system or when use of the MBAN system is permitted by a wireless communication system having an authority for the second frequency band.

The information related to each channel of the second frequency band may include a time when each channel is available.

Transmitting the information on the channel of the second frequency band to which the MBAN terminal is to be switched may comprise transmitting the information in a broadcast scheme.

The broadcast scheme may comprise transmitting the information through a beacon.

Transmitting the information on the channel of the second frequency band to which the MBAN terminal is to be switched may comprise transmitting the information in a unicast scheme.

The information on the channel of the second frequency band to which to be switched may include a recommended channel list.

The recommended channel list may have a form of a bitmap.

The information on the channel of the second frequency band to which to be switched may include one specific channel.

The information on the channel of the second frequency band to which to be switched may include one specific channel that is to be first searched and a list of channels to be searched when the specific channel is not searched.

The information on the channel of the second frequency band to which to be switched may include a time when the MBAN terminal is to perform channel switching.

The time when the MBAN terminal is to perform channel switching may be represented as a specific time value.

The time when the MBAN terminal is to perform channel switching may be represented as a predetermined time after the information on the channel to which to be switched is transmitted.

According to another embodiment of the present invention, an MBAN (Medical Body Area Network) master is provided.

The MBAN master comprises a controller controlling channel switching of an MBAN terminal using a channel of a first frequency band; and a wireless communication unit communicating with the MBAN terminal under the control of the controller, wherein the controller receives information related to use of each channel of a second frequency band from an MBAN controller and controls the wireless communication unit to transmit information on a channel of the second frequency band to which the MBAN terminal is to be switched based on the received information related to each channel of the second frequency band, and wherein the first frequency band and the second frequency band are separated from each other depending on whether the MBAN terminal may first use the MBAN system.

The information related to each channel of the second frequency band may include a time when each channel is available.

The controller may control the wireless communication unit to transmit the information on the channel of the second frequency band to which the MBAN terminal is to be switched in a broadcast scheme.

The broadcast scheme may comprise transmitting the information through a beacon.

The controller may control the wireless communication unit to transmit the information on the channel of the second frequency band to which the MBAN terminal is to be switched in a unicast scheme.

The information on the channel of the second frequency band to which to be switched may include a recommended channel list.

The information on the channel of the second frequency band to which to be switched may include one specific channel.

The information on the channel of the second frequency band to which to be switched may include one specific channel that is to be first searched and a list of channels to be searched when the specific channel is not searched.

The information on the channel of the second frequency band to which to be switched may include a time when the MBAN terminal is to perform channel switching.

Advantageous Effects

According to an embodiment of the present invention, an MBAN system may efficiently communicate with another wireless communication system without collisions. Accordingly, an MBAN terminal and an MBA master may perform communication more stably.

BRIEF DESCRIPTION OF DRAWINGS

FIG. 4 is a view illustrating a structure of a beacon frame used in an IEEE 802.15.4 system.

FIGS. 8(a) to 8(c) are views each illustrating a portion of a frame including channel switching information according to embodiments of the present invention.

FIG. 9 is a view illustrating a beacon frame according to an embodiment of the present invention.

FIG. 10 is a view illustrating a portion of a channel switching indicating command according to an embodiment of the present invention.

BEST MODE

Figure 1:
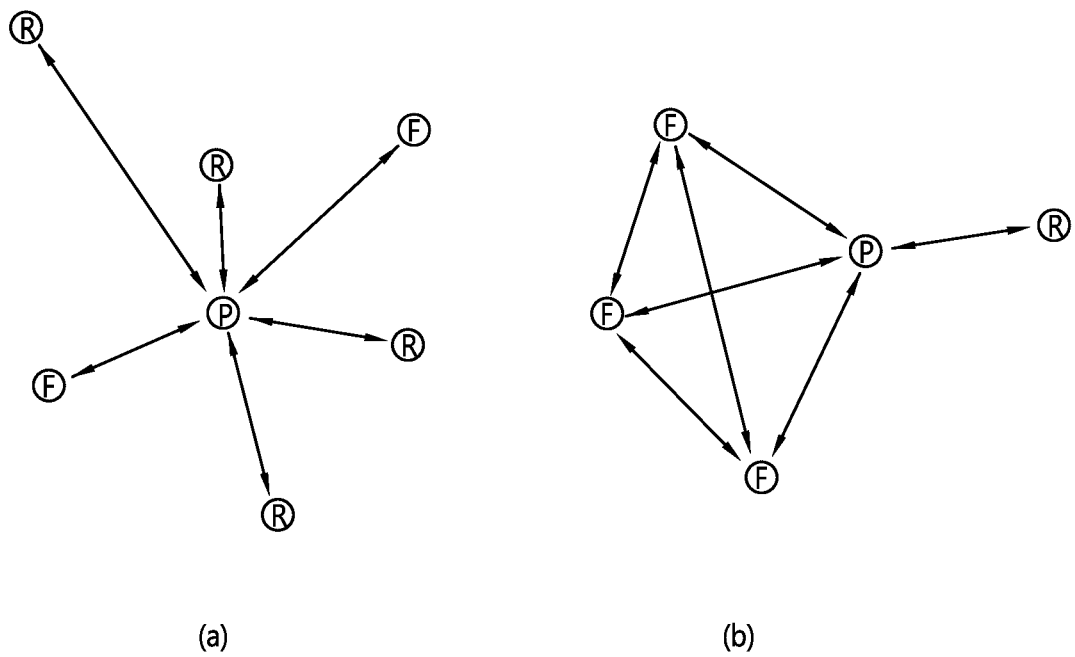
FIG. 1 illustrates an example of an IEEE 802.15.4-based network topology.

As used herein, the technical terms are used merely to describe predetermined embodiments and should not be construed as limited thereto. Further, as used herein, the technical terms, unless defined otherwise, should be interpreted as generally understood by those of ordinary skill in the art and should not be construed to be unduly broad or narrow. Further, when not correctly expressing the spirit of the present invention, the technical terms as used herein should be understood as ones that may be correctly understood by those of ordinary skill in the art. Further, the general terms as used herein should be interpreted as defined in the dictionary or in the context and should not be interpreted as unduly narrow.

As used herein, the singular form, unless stated otherwise, also includes the plural form. As used herein, the terms "including" or "comprising" should not be interpreted as necessarily including all of the several components or steps as set forth herein and should rather be interpreted as being able to further include additional components or steps.

Further, as used herein, the suffixes "module" or "unit" as used for components are mixed up for ease of drafting this disclosure and do not have separate or distinguished meanings or functions from each other.

Further, as used herein, the terms "first" and "second" may be used to describe various components, but these components are not limited thereto. The terms are used only for distinguishing one component from another. For example, without departing from the scope of the present invention, a first component may also be referred to as a second component, and the second component may likewise be referred to as the first component.

Hereinafter, preferred embodiments of the present invention will be described in detail with reference to the accompanying drawings. The same reference numerals may refer to the same or similar elements throughout the specification and the drawings.

When determined to make the gist of the present invention unclear, the detailed description of the present invention is skipped. Further, the accompanying drawings are provided merely to give a better understanding of the spirit of the present invention, and the present invention should not be limited thereto.

FIG. 1 illustrates an example of an IEEE 802.15.4-based network topology.

Two types of devices, such as an FFD (Full Function Device) and an RFD (Reduced Function Device), may participate in the IEEE 802.15.4 network. The FFD performs functions such as initialization of the network, node management, or storing node information. An FFD that allows the other devices to configure a network is referred to as a "PAN (Personal Area Network) coordinator."

The FFD is a device that may perform a coordinator function, and this device may configure various types of network topologies. The FFD may communicate with an FFD and the RFD both. The FFD consumes relatively much power to perform the coordinator function and thus is usually wiredly powered.

In contrast, the RFD is a device that cannot perform the coordinator function and is a target that is to be coordinated by the FFD. In other words, the RFD communicates with only the FFD and the FFD is fully in charge of networking functions. Accordingly, a minimum size of stack structure may be used, and computation/memory resources may be saved. Therefore, right after discovering a PAN coordinator and transmitting data to it, the RFD may disconnect itself therefrom and enter into a saving (sleep) mode, resulting in much less power consumption and prolonged battery use.

In FIG. 1, "F" denotes the FFD, "R" denotes the RFD, and "P" denotes the PAN coordinator.

FIG. 1 illustrates two types of network topologies that may be created by the IEEE 802.15.4 system. (a) of FIG. 1 illustrates an example of a star network, and (b) of FIG. 1 illustrates an example of a peer-to-peer network.

In the star topology, communication is performed only between the devices and the PAN coordinator. At this time, the devices are start and end points of the communication, while the PAN coordinator may be a start point, an end point, or a router.

In the peer-to-peer topology, each device may communicate with any of the other devices in the network. Accordingly, a more complicated network may be configured such as a mesh network.

The star network may operate devices so that their battery life lasts long. The peer-to-peer network may configure one or more data delivery paths, thus providing for high data reliability and access recognition rate.

Figure 2:
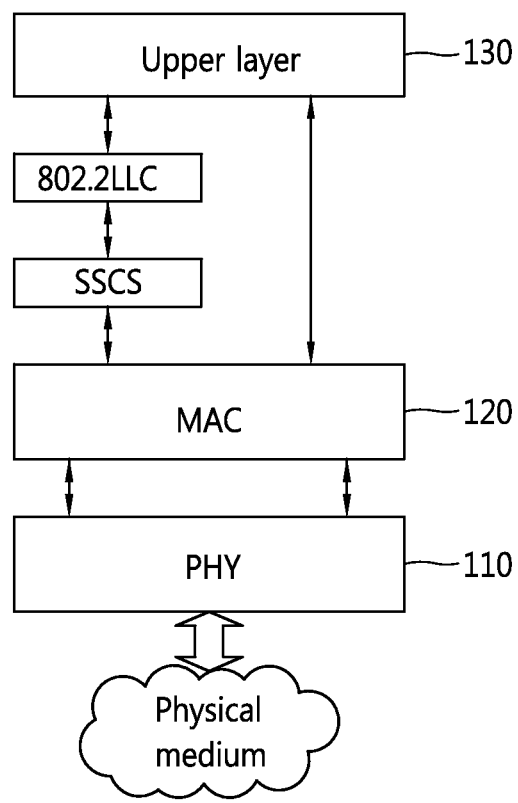
FIG. 2 illustrates a protocol stack structure in an IEEE 802.15.4 system.

FIG. 2 illustrates a protocol stack structure in an IEEE 802.15.4 system.

As can be seen from FIG. 2, the IEEE 802.15.4 protocol stack consists of a PHY (physical) layer 110, an MAC (Medium Access Control) layer 120, and an upper layer 130.

The PHY layer 110 includes an RF transceiver and its related control mechanism. The MAC layer 120 provides access to a physical channel for data transmission.

The upper layer 130 consists of a network layer and an application layer. The network layer provides functions, such as configuration, processing, or message routing of the network. The application layer provides a function the device aims for. By way of example, the IEEE 802.15.4 device 100 may function as an RFD (Reduced Function Device), FFD (Full Function Device), or coordinator depending on the type of a program mounted therein, that is, depending on the type of a program for processing the data of the application layer.

Figure 3:
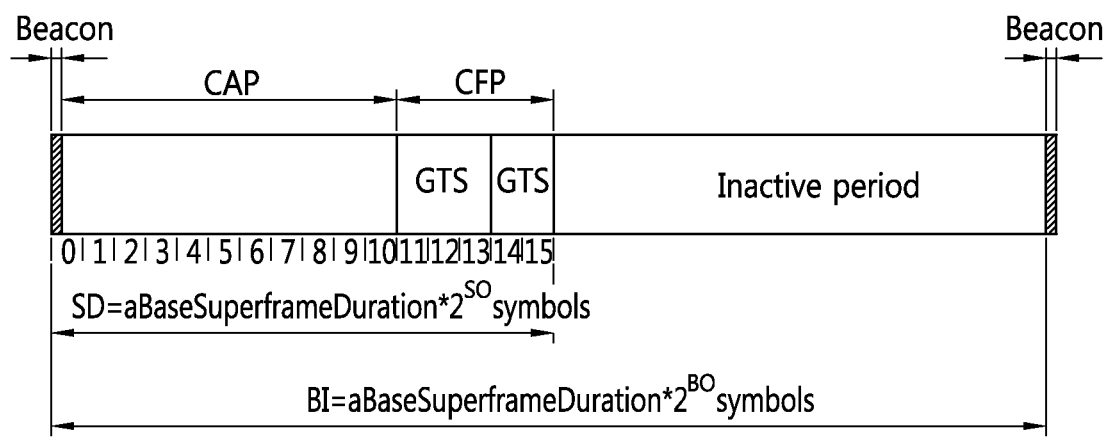
FIG. 3 is a view illustrating a structure of a super frame used in an IEEE 802.15.4 system.

FIG. 3 is a view illustrating a structure of a super frame used in an IEEE 802.15.4 system.

The IEEE 802.15.4 system includes a communication period (active period) and an inactive period depending on low-power requirements. The repetition cycle of the active period and the inactive period is referred to as "duty cycle."

The active period includes a beacon, a CAP (Contention Access Period), and a CFP (Contention Free Period) and data transmission primarily occurs in the CAP.

The CFP includes GTSs (Guaranteed Time Slots) and each GTS may be assigned to a specific device so that the GTS may be used for the device to transmit and receive data with a PAN coordinator. Up to seven GTSs may be supported in one PAN.

What is allocated for each GTS is configured in the form of a GTS descriptor by the PAN coordinator. The GTS descriptors are included in the GTS field of the beacon and are transmitted by the PAN coordinator.

FIG. 4 is a view illustrating a structure of a beacon frame used in an IEEE 802.15.4 system.

Each field of the beacon frame follows what is defined in IEEE 802.15.4.

In particular, what is allocated for each GTS is configured by the PAN coordinator in the form of a GTS descriptor. The GTS descriptors are included in the GTS field of the beacon and are transmitted by the PAN coordinator.

Figure 5:
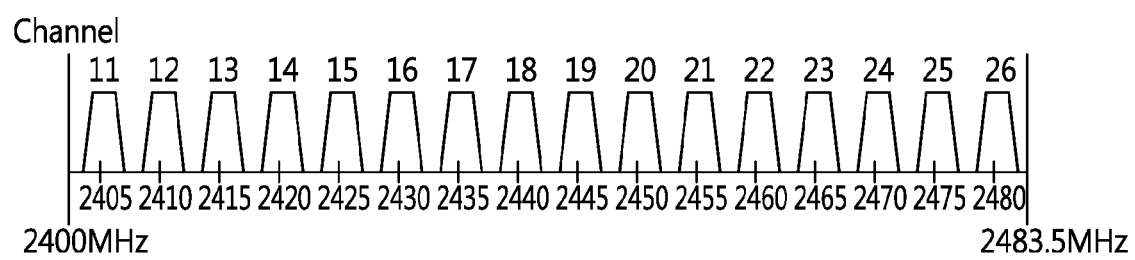
FIG. 5 is a view illustrating a channel arrangement of an IEEE 802.15.4 system.

FIG. 5 is a view illustrating a channel arrangement of an IEEE 802.15.4 system.

As can be seen in FIG. 5, the IEEE 802.15.4 system operating in a band of 2400 MHz has a channel spacing of 5 MHz.

An MBAN system based on the IEEE 802.15.4 system uses a band of 2360 to 2390 MHz and a band of 2390 to 2400 MHz. The band of 2360 to 2390 MHz may be used when the MBAN terminal in the healthcare facility is allocated with a channel from the MBAN master and operates (hereinafter, "MBAN PAN coordinator," "PAN coordinator," and "MBAN coordinator" have the same meaning). The band of 2390 to 2400 MHz is used when the MBAN terminal cannot receive information on the MBAN channel from the MBAN coordinator any longer or when the MBAN terminal and the coordinator operate outside the healthcare facility. Further, the band of 2390 to 2400 MHz may also be used as a basic channel band of the MBAN system.

Figure 6:
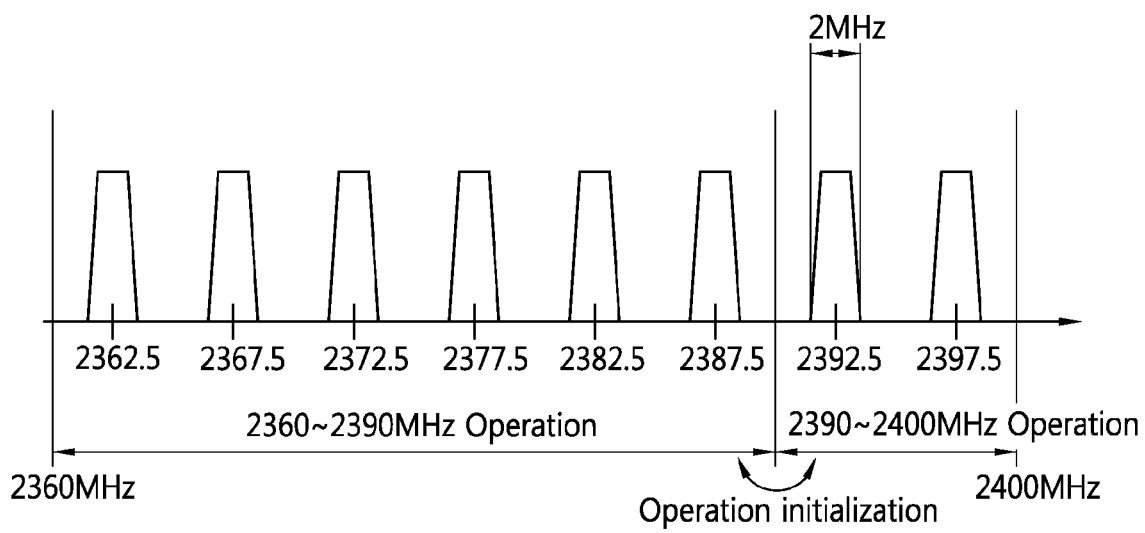
FIG. 6 is a view illustrating an example of a channel arrangement of an MBAN system.

FIG. 6 is a view illustrating an example of a channel arrangement of an MBAN system.

Channels of the MBAN available in a band of 2360 to 2400 MHz are marked in FIG. 6. The MBAN terminal operating in the band sometimes shifts a channel having a band of 2360 to 2390 MHz to a channel having a band of 2390 to 2400 MHz or vice versa. For example, when a user (primary user) of a wireless communication system except for an MBAN system having a priority in use of a corresponding band should use a channel having a band of 2360 to 2390 MHz, the terminal of the MBAN system should change its operation channel to a channel having a band of 2390 to 2400 MHz. In the above example, the MBAN terminal performs operation defaulting and changes the channels.

Hereinafter, a method of switching channels between a band of 2360 to 2390 MHz and a band of 2390 to 2400 MHz is described.

Figure 7:
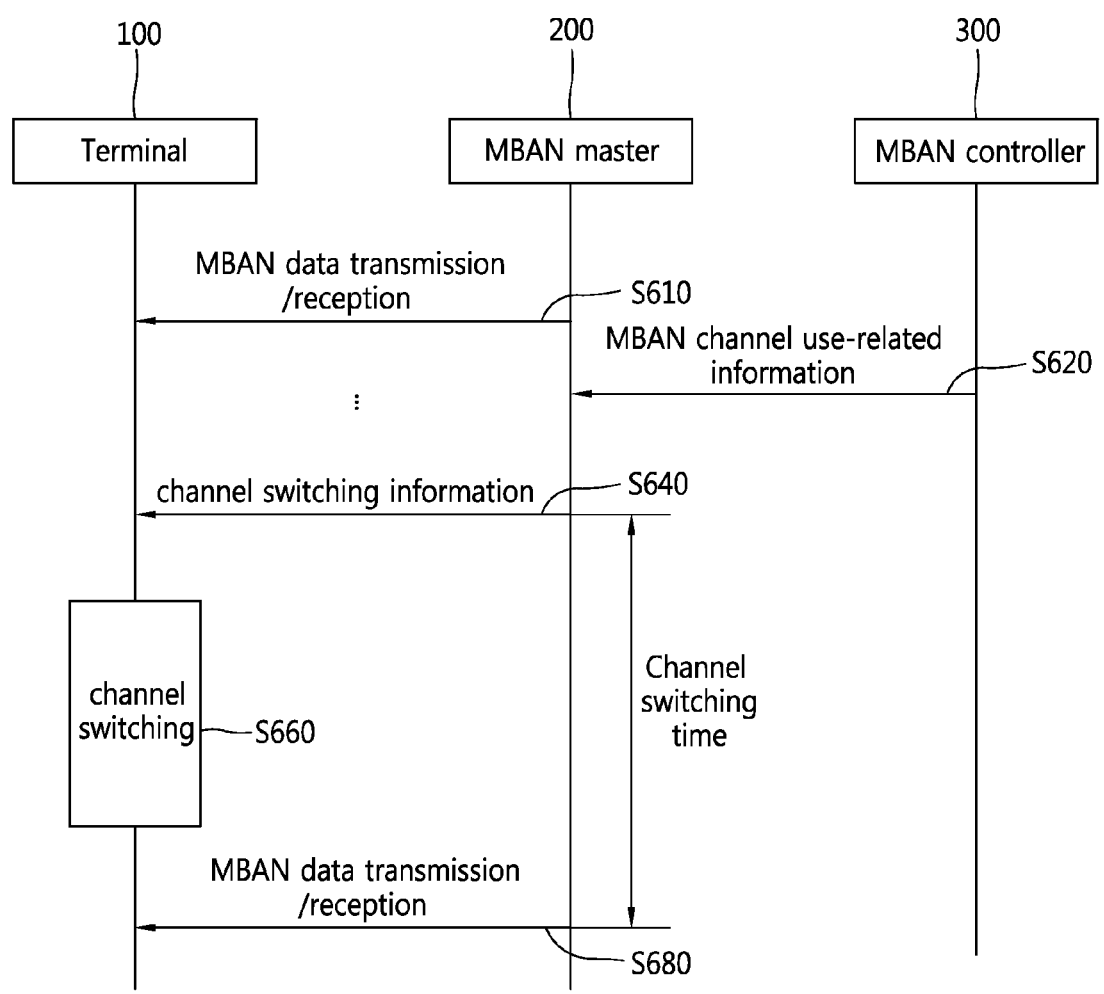
FIG. 7 is a flowchart illustrating an MBAN channel switching method according to an embodiment of the present invention.

FIG. 7 is a flowchart illustrating an MBAN channel switching method according to an embodiment of the present invention.

An MBAN master 200 and an MBAN terminal 100 perform communication using one of a channel having band of 2360 to 2390 MHz or a channel having a band of 2390 to 2400 MHz (S610). At this time, the MBAN master 200 and the MBAN terminal 100 sometimes need to switch their used channels to a channel having a different frequency band.

First, an example where the operation channel is switched from a channel having a band of 2360 to 2390 MHz to a channel having a band of 2390 to 2400 MHz is described. At this time, the band of 2360 to 2390 MHz is referred to as a first frequency band, and the band of 2390 to 2400 MHz is referred to as a second frequency band. As described above, the first frequency band the second frequency band are classified based on whether the MBAN terminal may first use the corresponding frequency band.

In case while the MBAN master 200 and the MBAN terminal 100 communicate with each other using the channel of the first frequency band, a primary user of a wireless communication system except for the MBAN system should use the first frequency band or when the MBAN terminal moves out of a designated area, for example, outside the healthcare facility, the MBAN master 200 and the MBAN terminal 100 switch the channel of the second frequency band and then transmit/receive data using the switched channel.

An example in which the operation channel is switched from the channel having a band of 2390 to 2400 MHz to the channel having a band of 2360 to 2390 MHz is now described. At this time, the band of 2390 to 2400 MHz is referred to as a first frequency band, and the band of 2360 to 2390 MHz is referred to as a second frequency band. As described above, the first and second frequency bands are classified depending on whether the MBAN terminal may first use the corresponding frequency band.

Under the situation in which the MBAN master 200 and the MBAN terminal 100 communicate with each other using the channel of the first frequency band, when the primary user of the wireless communication system except for the MBAN system terminates use of the second frequency band or for other reasons happens to be able to use the second frequency band (for example, when a wireless communication system having an authority for the second frequency band permits the MBAN system to use it), the MBAN master 200 and the MBAN terminal 100 may switch to the channel of the second frequency band and may then perform transmission/reception of data using the switched channel.

Information on the channel status of each frequency band as described above, that is, information indicating which and when channels of the band of 2360 to 2390 MHz and band of 2390 to 2400 MHz of the MBAN may be available is collected and managed by an MBAN controller 300.

The MBAN controller 300 may include a DB (database) that stores and manages the channel status of each frequency band, an MBAN coordinator that manages the DB, and an MBAN control point. A plurality of MBAN control points may be present under one MBAN coordinator, and each MBAN control point may control one or more MBAN masters. The MBAN control point may be functionally implemented in the MBAN coordinator or may be implemented as separate hardware or software that is physically separated from the MBAN coordinator.

In case the above-described channel switching is needed, information related to each channel of a frequency band (second frequency band) to which to be switched is delivered from the MBAN controller 300 to the MBAN master 200 (S620). At this time, information related to use of each channel of the second frequency band may be transferred from the MBAN coordinator through the MBAN control point to the MBAN master 200. In such case, the channel status information may be delivered in the form of an electronic key as set forth in the FCC (Federal Communications Commission) from the MBAN coordinator to the MBAN control point.

When receiving the information related to each channel of the second frequency band from the MBAN controller 300, the MBAN master 200 transmits information for the channel of the second frequency band to which the MBAN terminal 100 is switched based on the information related to each channel (S640). The information on the channel of the second frequency band to which the terminal is to switch may include a channel to which to be switched, time of the switching, and a frequency band where the channel switching is performed, and detailed description thereof will be made with reference to FIG. 8.

The information on the channel of the second frequency band to which the MBAN terminal is to switch may be transmitted to the MBAN terminal 100 in a broadcast scheme or in a unicast scheme. The broadcast scheme may be performed in such a manner that the corresponding information is included in the beacon frame and is transmitted. The unicast scheme may be performed with a command and a frame for channel switching separately defined.

When receiving the information on the channel of the second frequency band to which to be switched from the MBAN master 200, the MBAN terminal 100 performs channel switching based on the received information (S660). When completing the channel switching at a designated time, the MBAN terminal 100 transmits/receives data with the MBAN master 200 through a changed channel (S680).

FIGS. 8(*a*) to 8(*c*) are views each illustrating a portion of a frame including channel switching information according to embodiments of the present invention.

The channel switching information is information for a channel of a different frequency band (second frequency band) to which to be switched as transmitted from the MBAN master 200 to the MBAN terminal 100.

The information on the channel of the second frequency band to which to be switched may include a channel to which to be switched, time for switching, and a frequency band where channel switching is performed. The channel to which to be switched may be a specific channel, a list of recommended channels, or a combination thereof. The time for switching may be represented as an absolute time such as a coordinated universal time or in an indirect manner as a time difference from a specific time.

FIG. 8(*a*) illustrates an example of information on a channel of a second frequency band to which to be switched.

In FIG. 8(*a*), the channel switching method field represents whether the MBAN terminal is to switch from the band of 2390 to 2400 MHz to the band of 2360 to 2390 MHz or from the band of 2360 to 2390 MHz to the band of 2390 to 2400 MHz.

The recommended channel list field represents a channel to which to be switched among the channels belonging to the second frequency band to which to be switched. At this time, the recommended channel list may be represented in the form of a bitmap for all of the channels of the band of 2360 to 2390 MHz and band of 2390 to 2400 MHz. By doing so, which channel the MBAN terminal is recommended to be switched to may be represented. The size of the bitmap is determined in accordance with the number of available channels of the MBAN. In case each bit represents one MBAN channel and is '0,' it represents that switching to the corresponding channel is impossible, and in case each bit is '1,' it represents that switching to the corresponding channel is possible. The MBAN terminal may switch to one of the channels indicated with '1.'

The whole bitmap being denoted with 'Os' does not mean that none of the channels may be used. In this case, if there is channel information transferred in other ways, switching to the channel is performed, and otherwise, the MBAN terminal searches all of the channels and should select a valid channel to which to be switched. The valid channel means a channel to which the MBAN terminal may access and through which a signal from the MBAN master is transmitted.

For the MBAN master to indicate channel switching using the recommended channel list, the MBAN terminal should be aware of information on the channels present in the second frequency band to which the MBAN terminal is to switch.

The remaining time field denotes a time when the MBAN terminal should perform channel switching. At this time, the remaining time value may be expressed in the form of an absolute time in which a specific time is directly represented or in the form of indicating that channel switching should be performed a predetermined time after information on the channel of the second frequency band to which to be switched has been transmitted. In case the remaining time value is represented in the "after the predetermined time" form, when the remaining time field value is 0, this means that channel switching should be done immediately.

FIG. 8(b) illustrates another example of information on a channel of a second frequency band to which to be switched.

In the example illustrated in FIG. 8(b), unlike FIG. 8(a), the MBAN master designates one specific channel as the channel to which to be switched through a channel number. Other field values are the same as those shown in FIG. 8(a).

FIG. 8(c) illustrates another example of information on a channel of a second frequency band to which to be switched.

In the example of FIG. 8(b), the MBAN master transmits the recommended channel list field and the channel number field both to the MBAN terminal. In such case, the MBAN terminal searches the specific channel designated by the channel number field for channel switching. If a signal of the MBAN master is not searched in the specific channel designated in the channel number field, the channels designated in the recommended channel list field are searched.

FIG. 9 is a view illustrating a beacon frame according to an embodiment of the present invention.

When the MBAN master 200 transmits information on a channel to which to be switched to the MBAN terminal 100, a broadcast scheme may be used. At this time, the broadcast scheme may be conducted in such a manner that the corresponding information is included in the beacon frame and is transmitted. As can be seen from FIG. 9, the MBAN master 200 may transmit the beacon frame defined in IEEE 802.15.4, including a channel switching method field, a recommended channel list field and a remaining time field therein. When receiving the beacon including the fields, the MBAN terminal may conduct channel switching as described above in connection with FIGS. 7 and 8.

FIG. 10 is a view illustrating a portion of a channel switching indicating command according to an embodiment of the present invention.

When the MBAN master 200 transmits information on a channel to which to be switched to the MBAN terminal 100, a unicast scheme may be used. The unicast scheme may be performed with a command and a frame for channel switching separately defined. FIG. 10 illustrates an example of such a channel switching command, which includes a channel switching method field, a recommended channel list field, and a remaining time field. When receiving the channel switching command including the fields, the MBAN terminal may perform channel switching as described above in connection with FIGS. 7 and 8.

Figure 11:
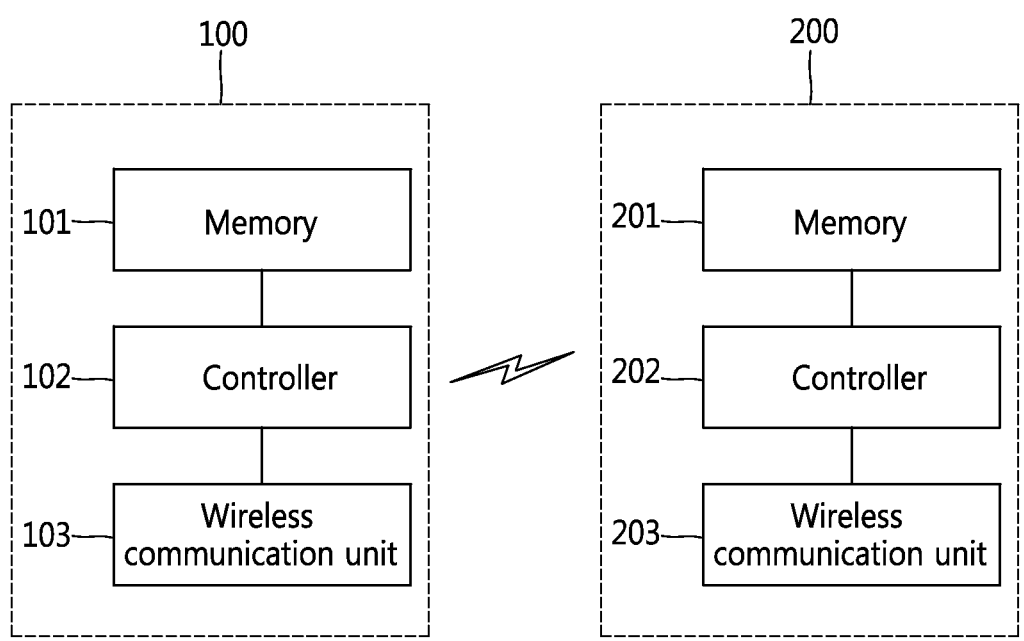
FIG. 11 is a block diagram illustrating an MBAN terminal and an MBAN master according to an embodiment of the present invention.

FIG. 11 is a block diagram illustrating an MBAN terminal and an MBAN master according to an embodiment of the present invention.

The MBAN terminal 100 may include a memory 101, a controller 102, and a wireless communication unit 103.

The memory 101 may store the methods suggested herein. The memory 101 may also store channel group identifiers received under the control of the controller 102. The memory 101 may store a preset channel group and channels included in the channel group.

The controller 102 controls the overall operation of the MBAN terminal and controls the memory 101 and the wireless communication unit 103. The controller 102 may receive information on a channel of a different frequency band (second frequency band) to which to be switched from the MBAN master. At this time, the information on the second frequency band to which to be switched may include a frequency band to which the channel to which to be switched belongs, a specific channel or a channel list, and a time for switching.

The controller 102 may control the channel switching based on the received information on the channel of the second frequency band to which to be switched.

The wireless communication unit 103 may explore a channel of the MBAN system under the control of the controller 102 and may switch operation channels. At this time, the wireless communication unit 103 may explore one specific channel or may sequentially explore a plurality of channels.

The MBAN master 200 may include a memory 201, a controller 202, and a wireless communication unit 203.

The memory 201 may store the methods suggested herein. The memory 201 may store information related to use of the channels of the MBAN frequency band under the control of the controller 202. That is, the memory 201 may store information such as the state of use of each channel or available time.

The controller 102 controls the overall operation of the MBAN master 200 and controls the memory 101 and the wireless communication unit 103. The controller 102 may receive information related to use of each channel of an MBAN frequency band from the MBAN controller. The controller 102 may generate information on a channel to which the MBAN terminal is to be switched based on the received information and may transmit the generated information to the MBAN terminal. At this time, the information on the channel to which to be switched may include a frequency band to which the channel to which to be switched belongs, a specific channel or a channel list, and a time for switching.

The controller 102 may transmit the information on the channel to which to be switched in a broadcast scheme or in a unicast scheme. In case the information is transmitted in the broadcast scheme, the controller 102 may transmit the information including the information on the channel to which to be switched in a beacon frame.

The wireless communication unit 203 may communicate with the MBAN terminal through a designated channel under the control of the controller 102. Further, the wireless communication unit 203 may transmit beacon and command frames through a physical channel under the control of the controller 102.

The various embodiments set forth herein may be implemented in a recording medium that may be read by a computer or a similar device using software, hardware, or a combination thereof.

Although embodiments of the present invention have been described, it will be understood by those of ordinary skill that various changes and modifications can be made thereto without departing from the scope of the present invention defined by the appended claims.

The invention claimed is:

1. A method for channel switching in a wireless communication system that supports medical body area network (MBAN) services and operates in the 2360 MHz-2400 MHz frequency band, the method comprising:
    determining, by an MBAN coordinator, whether a primary user is scheduled to use an operating channel that is currently used by an MBAN master device and an MBAN device for communication between the MBAN master device and the MBAN device; and
    when the first MBAN coordinator determines that the primary user is scheduled to use the operating channel, transmitting, by the MBAN coordinator, first channel switching information to protect the primary user,
    wherein the first channel switching information is transmitted to the MBAN master device, wherein the first channel switching information includes a first remaining time field and a first channel number field,
wherein the first remaining time field includes information on a first time when the channel switching occurs by the MBAN master device,
wherein the first time is determined based on a transmission time of the first channel switching information,
wherein the first channel number field includes information on a channel to be switched,
wherein the channel switching information further includes a first channel switching method field,
wherein the first channel switching method field includes information on a frequency band to be switched,
wherein the frequency band includes the channel to be switched,
wherein the MBAN master device transmits second channel switching information to the MBAN device,
wherein the second channel switching information is generated based on the first channel switching information by the MBAN master device,
wherein the second channel switching information includes a second remaining time field, a second channel number field, and a second channel switching method field,
wherein the second remaining time field includes information on a second time when the channel switching occurs by the MBAN device,
wherein the second time reaches 0 based on a transmission time of the second channel switching information,
wherein the channel number field includes the information on the channel to be switched,
wherein the channel switching method field includes information on the frequency band to be switched, and
wherein the second channel switching information is transmitted to the MBAN device based on a broadcast method via a beacon frame by the MBAN master device.

2. A medical body area network (MBAN) coordinator for channel switching in a wireless communication system that supports MBAN services and operates in the 2360 MHz-2400 MHz frequency band, the MBAN coordinator comprising:
a controller configured to determine whether a primary user is scheduled to use an operating channel that is currently used by an MBAN master device and an MBAN device for communication between the MBAN master device and the MBAN device; and
a wireless communication unit configured to transmit first channel switching information to the MBAN master device to protect the primary user when the controller determines that the primary user is scheduled to use the operating channel,
wherein the first channel switching information is transmitted to the MBAN master device,
wherein the first channel switching information includes a first remaining time field and a first channel number field,
wherein the first remaining time field includes information on a first time when the channel switching occurs by the MBAN master device,
wherein the channel number field includes information on a channel to be switched,
wherein the first channel switching information further includes a first channel switching method field indicating a frequency band to be switched,
wherein the frequency band includes the channel to be switched,
wherein the MBAN master device transmits second channel switching information to the MBAN device,
wherein the second channel switching information is generated based on the first channel switching information by the MBAN master device,
wherein the second channel switching information includes a second remaining time field, a second channel number field, and a second channel switching method field,
wherein the second remaining time field includes information on a second time when the channel switching occurs by the MBAN device,
wherein the second time reaches 0 based on a transmission time of the second channel switching information,
wherein the channel number field includes the information on the channel to be switched,
wherein the channel switching method field includes the information on the frequency band to be switched, and
wherein the second channel switching information is transmitted to the MBAN device based on a broadcast method via a beacon frame by the MBAN master device.

3. A method for channel switching in a wireless communication system that supports medical body area network (MBAN) services and operates in the 2360 MHz-2400 MHz frequency band, the method comprising:
receiving, by an MBAN master device, first channel switching information to perform a channel switching from an MBAN coordinator to protect the primary user that is scheduled to use an operating channel that is currently used by the MBAN master and an MBAN device to communicate with the first MBAN device;
transmitting, by the MBAN master device, second channel switching information to the MBAN device; and
performing, by the MBAN master device, the channel switching based on the first channel switching information,
wherein the first channel switching information includes a first remaining time field, a first channel number field, and a first channel switching method field,
wherein the first remaining time field includes information on a first time when the channel switching occurs by the MBAN master device,
wherein the first time is determined based on a transmission time of the first channel switching information,
wherein the first channel number field includes information on a channel to be switched,
wherein the first channel switching method field includes information on a frequency band to be switched,
wherein the second channel switching information includes a second remaining time field, a second channel number field, and a second channel switching method field,
wherein the second remaining time field includes information on a second time when the channel switching occurs by the MBAN device,
wherein the second time reaches 0 based on a transmission time of the second channel switching information,
wherein the channel number field includes the information on the channel to be switched, and
wherein the channel switching method field includes the information on the frequency band to be switched.

4. A medical body area network (MBAN) master device, the MBAN master device comprising:
a wireless communication unit configured to:
receive first channel switching information from an MBAN coordinator to perform a channel switching to protect the primary user that is scheduled to use an operating channel that is currently used by the MBAN master and an MBAN device; and transmit second channel switching information to the MBAN device; and a controller configured to perform the channel switching based on the first channel switching information, wherein the first channel switching information includes a first remaining time field, a first channel number field, and a first channel switching method field, wherein the first remaining time field includes information on a first time when the channel switching occurs by the MBAN master device, wherein the first time is determined based on a transmission time of the first channel switching information, wherein the first channel number field includes information on a channel to be switched, wherein the first channel switching method field includes information on a frequency band to be switched, wherein the second channel switching information includes a second remaining time field, a second channel number field, and a second channel switching method field, wherein the second remaining time field includes information on a second time when the channel switching occurs by the MBAN device, wherein the second time reaches 0 based on a transmission time of the second channel switching information, wherein the channel number field includes the information on the channel to be switched, and wherein the channel switching method field includes the information on the frequency band to be switched.

* * * * *